(12) United States Patent
Kratz et al.

(10) Patent No.: US 6,380,443 B1
(45) Date of Patent: Apr. 30, 2002

(54) PREPARATION OF 1,3-DIOLS

(75) Inventors: Detlef Kratz, Heidelberg; Harald Rust, Neustadt; Roland Krokoszinski, Weisenheim; Volker Helf, Eisenberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/677,862

(22) Filed: Oct. 3, 2000

(30) Foreign Application Priority Data

Oct. 6, 1999 (DE) .......................... 199 48 112

(51) Int. Cl.⁷ .................. C07C 27/04; C07C 31/18; C07C 45/00
(52) U.S. Cl. .................. 568/862; 568/461; 568/463; 568/464; 568/852
(58) Field of Search ................ 568/852, 862, 568/461, 463, 464

(56) References Cited

U.S. PATENT DOCUMENTS 4,021,497 A   5/1977   Adam et al. ............. 260/638
4,225,726 A  * 9/1980  Morris et al. ............ 560/238

FOREIGN PATENT DOCUMENTS

| JP | 1299-240 | 12/1989 |
| JP | 2040-333 | 2/1990 |
| WO | WO 95/07254 | 3/1995 |
| WO | WO-95/07254 * | 3/1995 |
| WO | WO 97/16401 | 5/1997 |

* cited by examiner

Primary Examiner—Samuel Barts
Assistant Examiner—Elvis O. Price
(74) Attorney, Agent, or Firm—Keil & Weinkauf

(57) ABSTRACT

A process for preparing 1,3-diols having 6 or more carbon atoms comprises a) provision of at least one alkanal having at least three carbon atoms; b) thermal treatment of the alkanal in the absence of a basic catalyst; c) hydrogenation of the aldol addition product formed in step b); and d) isolation of the 1,3-diol obtained.

Figure 1:
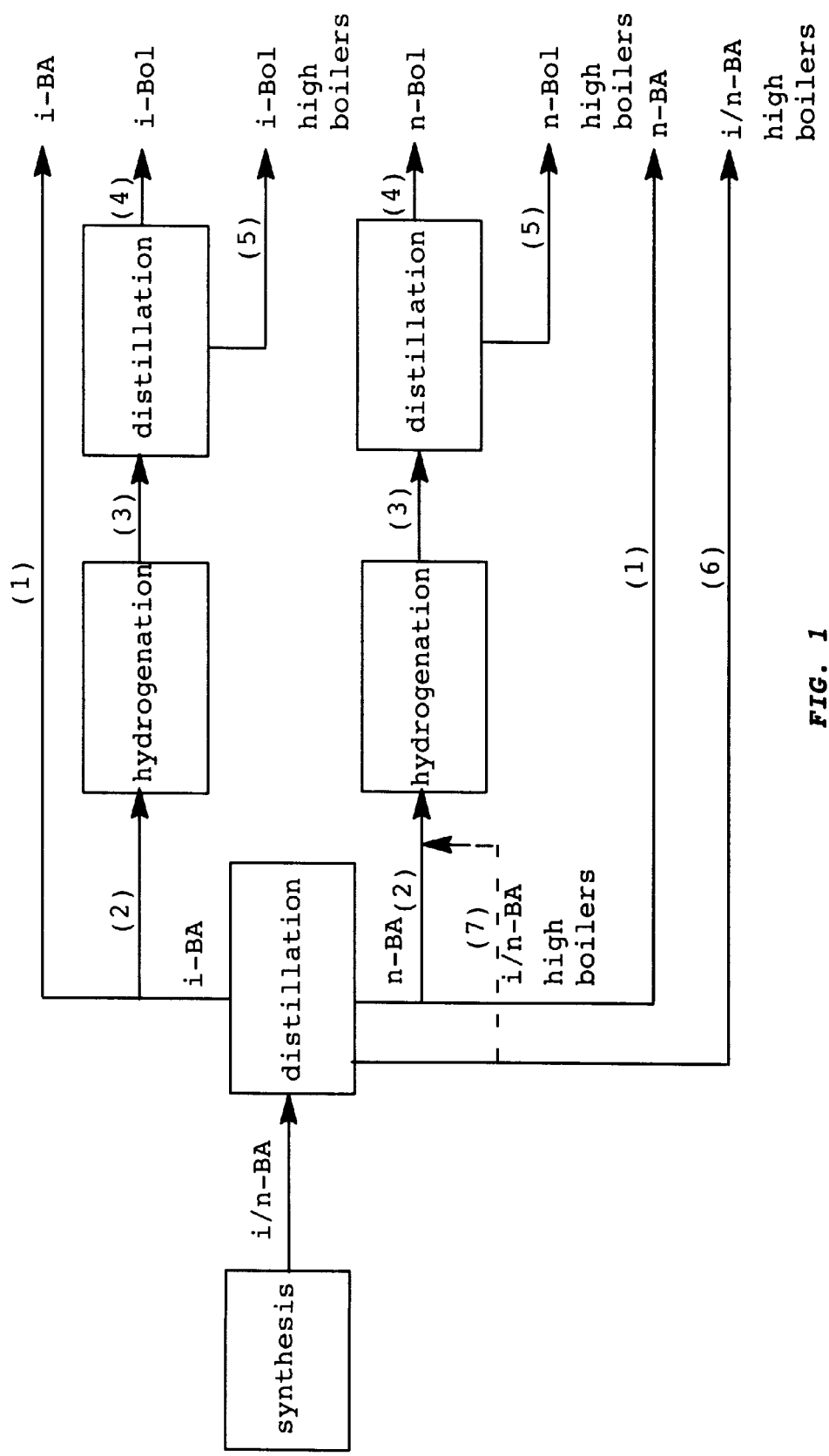

The process of the present invention makes it possible to prepare 1,3-diols simply and inexpensively.

10 Claims, 2 Drawing Sheets

PREPARATION OF 1,3-DIOLS

The present invention relates to a process for preparing 1,3-diols having 6 or more carbon atoms by means of the aldol reaction.

1,3-Diols having six or more carbon atoms in the basic skeleton are versatile starting materials in the chemical industry. They can be used, for example, in the production of polyesters, polyurethanes, coatings raw materials, dispersions and plasticizers.

Such materials include 1,3-diols having eight carbon atoms for example 2-ethylhexane-1,3-diol (EHD), 2,2-dimethylhexane-1,3-diol (DMHD), 2,2,4-trimethylpentane-1,3-diol (TMPD) and 2-ethyl-4-methylpentane-1,3-diol (EMPD). These materials are additionally used as insect repellents.

It is known from WO A 97/16401 that such 1,3-diols can be prepared by hydroformylation of an olefin to give the corresponding aldehyde, subsequent aldol reaction with a further aldehyde with addition of an aldol catalyst and subsequent hydrogenation.

Wo 95/07254 describes a process for producing EHD by base-catalyzed reaction of n-butyraldehyde (n-BA) in the presence of a phase transfer catalyst. The yield indicated there is about 56%.

The preparation of EHD by means of aldol addition is also described in JP 2040-333-A. Here, n-BA is reacted in the presence of NaOH or KOH in butanol to give a mixture of 2-ethyl-3-hydroxyhexanal, the dehydration product 2-ethylhexenal derived therefrom and higher-boiling aldol-like condensation products. The selectivity of this aldol reaction is 86% and the conversion achieved is about 58%. The resulting mixture is neutralized with acetic acid and subsequently subjected to catalytic hydrogenation over a Raney nickel catalyst.

JP-A 1299-240 describes a similar process in which sodium methoxide in butanol is used as catalyst.

U.S. Pat. No. 4,225,726 discloses the use of tin or tin oxide as catalyst for preparing the butyric ester of, for example, EHD.

However, the above-described processes have the following disadvantages:

The incomplete conversion of n-BA means that n-butanol is obtained as a significant by-product in the hydrogenation. Although n-BA could be separated off prior to the hydrogenation, this results in additional costs.

In addition, the known processes employ catalysts for the aldol reaction. If the aldol catalyst is still present in the subsequent steps, for instance a hydrogenation or distillation, the aldol addition product (2-ethyl-3-hydroxyhexanal when n-BA is used as starting material) can be redissociated; furthermore, 2-ethyl-3-hydroxyhexanal can also enter into yield-reducing secondary reactions. For this reason, complicated removal of the catalyst, for example by neutralization, washing and absorption, is necessary in this case in order to avoid losses in yield. The aldol catalyst can likewise impair the efficiency of the hydrogenation or even poison the hydrogenation catalyst.

The formation of the abovementioned dehydration product cannot be avoided in the presence of a catalyst and causes an additional loss in yield.

The route for preparing the diol via an ester, for example the preparation of EHD via the butyric ester described in U.S. Pat. No. 4,225,726, requires an additional process step. Although the saponification of the ester does give EHD, i.e. the desired diol, it also forms the acid component of the ester, e.g. butyric acid or a salt of butyric acid, as coproduct. The removal of such coproducts is once more associated with additional costs.

The aldol reaction also forms a series of by-products such as esters, ethers, aldoxanes, hemiacetals and acetals of the aldehyde which lead, after hydrogenation, to a broad spectrum of by-product. This in turn makes it considerably more difficult to isolate the pure diol by distillation.

It is an object of the present invention to provide a simple and inexpensive process for preparing 1,3-diols which, in particular, avoids or at least reduces the disadvantages of the abovementioned conventional processes.

We have found that this object is achieved by preparing 1,3-diols having 6 or more carbon atoms in a simple manner by thermal treatment of alkanals.

The present invention accordingly provides a process for preparing 1,3-diols having 6 or more carbon atoms, which comprises the following steps:

a) provision of at least one alkanal having 3 or more carbon atoms, b) thermal treatment of the alkanal in the absence of a basic catalyst, c) hydrogenation of the aldol addition product formed in step b) to give the 1,3-diol, and d) isolation of the 1,3-diol.

The process of the present invention starts out, as per step a), from at least one alkanal having three or more carbon atoms, in particular n-butyraldehyde and i-butyraldehyde. The alkanal can be provided by means of customary processes for preparing alkanals. The alkanal is preferably provided by means of the oxo process, in particular starting from ethylene or propylene. The oxo process is known, for example from Ullmann's Encyclopedia of Industrial Chemistry, Vol. A18, 321, $5^{th}$ Edition. In the oxo process, the olefin is reacted with carbon monoxide and hydrogen in the presence of a transition metal catalyst, generally rhodium or cobalt, under superatmospheric pressure and at elevated temperature. In the case of olefins having 3 or more carbon atoms, the oxo process generally gives a mixture of isomers of the corresponding alkanal. Thus, for example, the oxo process starting from propylene gives a mixture of i-butyraldehyde (i-BA) and n-butyraldehyde (n-BA). Depending on the process conditions, the ratio of i-BA to n-BA can vary from about 50/50 to 5/95. The process of the present invention can be carried out starting from one alkanal or a mixture of two or more alkanals of any composition, with the alkanals preferably having from 3 to 10 carbon atoms.

In step (b), the alkanal is subjected to a thermal treatment in the absence of a basic catalyst as is customarily used for an aldol addition. In the thermal treatment, a thermally induced aldol addition occurs to form the corresponding aldol addition product. The thermal treatment is preferably carried out during a distillation or hydrogenation of the alkanal. The crude product obtained in the provision of the alkanal can, for example, be subjected to a distillation to purify the alkanal or to fractionate an alkanal mixture. In the distillation, as mentioned, a thermally induced aldol addition occurs to form the corresponding aldol addition product. This has a higher boiling point than the corresponding alkanal and therefore accumulates in the high-boiling fraction obtained in the distillation. In order to obtain the 1,3-diol, the high-boiling fraction has to be subjected to a hydrogenation. This is carried out under the conditions customary for the hydrogenation of alkanals, i.e. in the presence of a hydrogenation catalyst, for example as described in DE 12 69 605, in the liquid or gas phase. Examples of suitable catalysts are copper chromite, supported nickel, copper or cobalt catalysts which may be doped with, for example, Mo, Mn or Cr, with suitable support materials being, for example, silica, kieselguhr, carbon, zirconium oxide, silicon carbide and the like. Further suitable catalysts are catalysts comprising noble metals such as Pd, Pt or Rh. The pressure at which the hydrogenation is carried out is preferably in the range from 1 to 250 bar, in particular from 10 to 150 bar. The temperature is generally in the range from 50 to 250° C., in particular from 100 to 210° C. The high-boiling fraction comprising the aldol addition product is preferably hydrogenated together with the alkanal.

In a further embodiment, the thermal treatment is carried out during a hydrogenation of an alkanal. The hydrogenation is carried out under the abovementioned conditions, resulting in formation of the aldol addition product. This aldol addition product is at the same time reduced to the 1,3-diol. The hydrogenation of a pure alkanal gives the corresponding 1,3-diol, while hydrogenation of an alkanal mixture gives a mixture of the corresponding 1,3-diols.

In step c), the 1,3-diol is then isolated in a customary manner. This is preferably achieved by distillation of the 1,3-diol-containing product obtained in the hydrogenation. The low-boiling fraction, namely the alkanol formed in the hydrogenation of the alkanal, is distilled off, with the 1,3-diol accumulating in the high-boiling fraction. The latter is subjected to a further distillation in which the 1,3-diol is distilled off and can surprisingly be obtained in pure form despite the large number of secondary components. The distillation can be carried out continuously or batchwise. The distillation conditions depend on the 1,3-diol concerned. The distillation is preferably carried out using a column. Particularly suitable columns are packed columns which have lower differential pressures than do columns provided with bubble cap trays or valve trays. This minimizes the thermal stress on the product to be distilled, so that essentially no decomposition reactions are observed in the bottom of the column. A decomposition reaction can lead to low-boiling impurities in the 1,3-diol. In general, the distillation is carried out under reduced pressure, for example at a pressure in the range from 1 to 500 mbar, preferably from 5 to 250 mbar and in particular from 10 to 100 mbar. The distillation temperature depends on the pressure selected and on the 1,3-diol concerned, although the temperature at the bottom should be not more than 2000° C.

Figure 2:
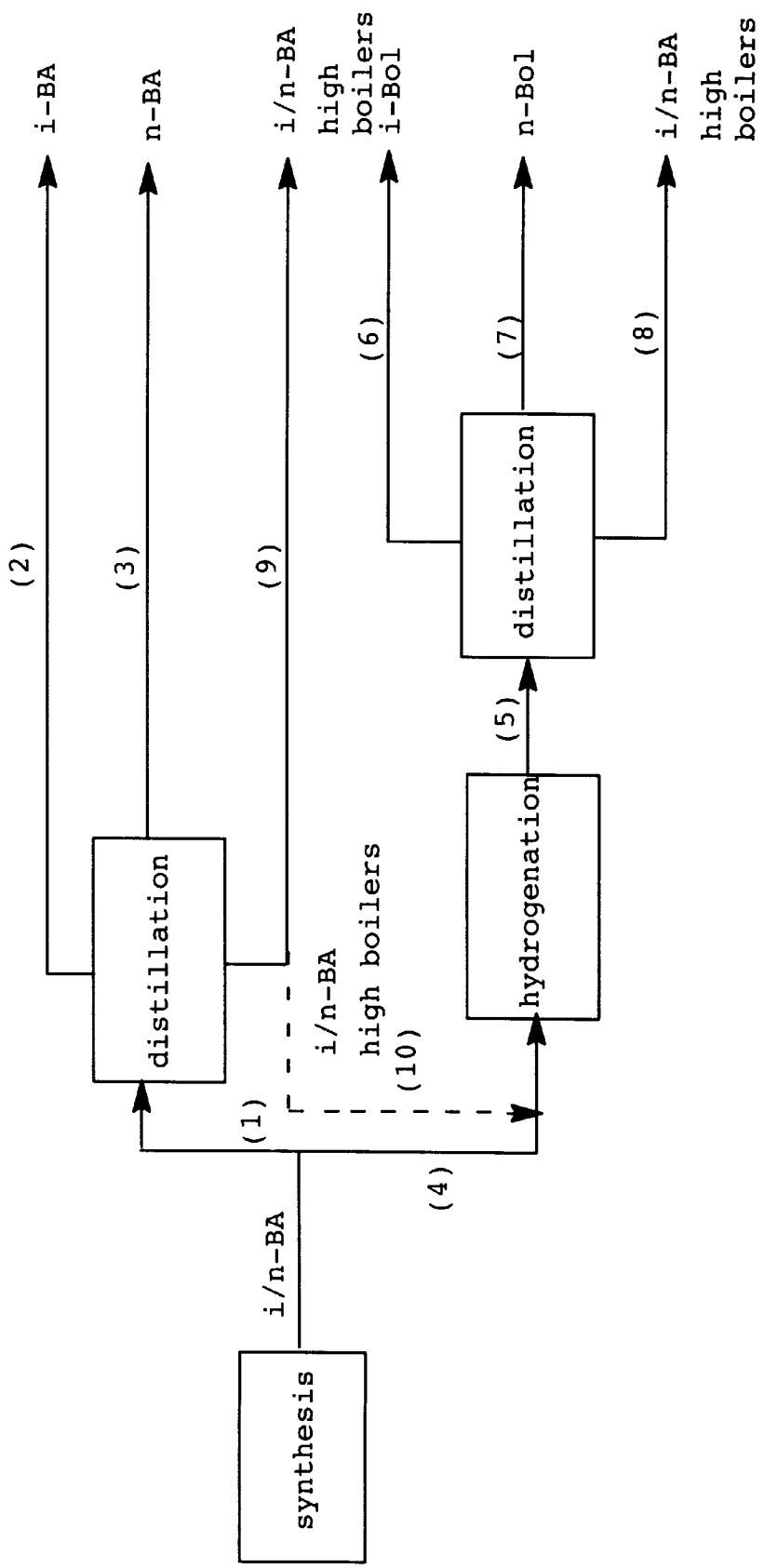

In the following, the process of the present invention is illustrated with reference to FIGS. 1 and 2. FIGS. 1 and 2 each schematically show an embodiment of the process of the present invention. i-Butyraldehyde and n-butyraldehyde are used as examples of alkanals for the purposes of this discussion. In the embodiment shown in FIG. 1, the crude mixture of i-butyraldehyde and n-butyraldehyde, as is obtained, for example, from propylene in the oxo process, is first separated by distillation into the i- and n-butyraldehydes. Any proportion can be taken off as pure aldehyde, cf. streams (1). The remainder of the pure aldehydes is subjected to a hydrogenation to give the corresponding alcohols, cf. streams (2). The hydrogenation is carried out under the above-described conditions. In the hydrogenation, the aldol addition product is formed and is at the same time reduced to the corresponding 1,3-diol.

The product from the hydrogenation is then passed to a distillation (cf. streams (3)) in order to isolate the alcohol formed, namely n-butanol or i-butanol (n-Bol or i-Bol). This is indicated by the streams (4). The distillation is carried out in a customary manner in one or more columns, for example using a packed column. Pressure and temperature depend on the alcohol concerned.

The 1,3-diol accumulates in the high-boiling fraction from the distillation, when using a column in the bottoms, cf. streams (5). The 1,3-diol can be isolated in a customary manner from these high-boiling fractions, for example by distillation under the abovementioned conditions. In this embodiment, the aldol addition product is formed from a single alkanal. This then gives a single corresponding 1,3-diol, namely EHD from n-butyraldehyde and TMPD from i-butyraldehyde. Alternatively, the high-boiling fraction from the distillation of the crude alkanal mixture, cf. stream (6), which comprises a mixture of aldol addition products, can be subjected to hydrogenation in order to obtain a 1,3-diol. However, the hydrogenation is preferably carried out together with the hydrogenation of an alkanal, for example together with the hydrogenation of n-butyraldehyde, cf. stream (7).

In FIG. 2, part of the crude alkanal mixture obtained from propylene in the oxo process is subjected to a distillation to isolate the pure aldehydes, cf. streams (1), (2) and (3). The remainder of the crude mixture is subjected to hydrogenation under the abovementioned conditions. Analogously to the embodiment of FIG. 1, the aldol addition product is formed and at the same time is hydrogenated to give the corresponding 1,3-diol, cf. stream (4). The product of the hydrogenation is then subjected to a distillation, for example a distillation in a column or a plurality of columns as described above. In this distillation, n-butanol and i-butanol are distilled off and separated and taken off, cf. streams (6) and (7). The 1,3-diol accumulates in the high-boiling fraction from the distillation, in the case of a distillation in a column in the bottoms. To isolate the 1,3-diol, the high-boiling fraction is in turn subjected to a distillation, which is carried out under the abovementioned conditions.

Alternatively, the high-boiling fraction obtained in the distillation of the aldehyde mixture (cf. stream (9)), which likewise comprises the aldol addition product, can be subjected to hydrogenation and distillation to isolate the 1,3-diol. Preferably, the high-boiling fraction is hydrogenated together with the aldehyde mixture, cf. stream (10), and worked up further as described above.

The amount of 1,3-diols formed is from about 40 to 60% by weight of the high-boiling fraction.

In the embodiment shown in FIG. 2, a mixture of i- and n-butyraldehydes is thermally treated, as stated above. This therefore results in all combinations of aldol addition products, namely i/i, n/i, i/n, n/n. The hydrogenation then gives a mixture of the corresponding 1,3-diols. This is shown by the reaction equations below.

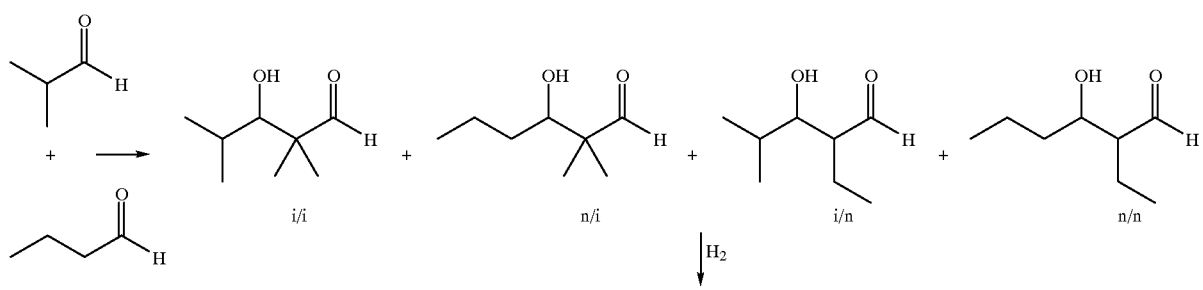

-continued

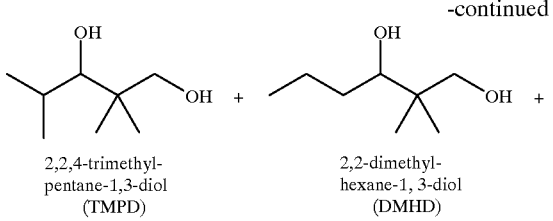
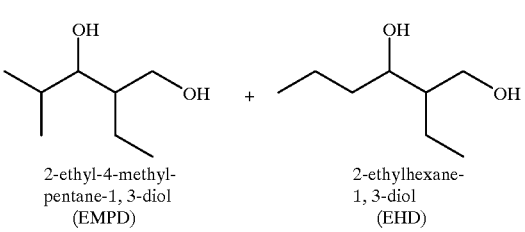

2,2,4-trimethyl-pentane-1,3-diol (TMPD)

2,2-dimethyl-hexane-1,3-diol (DMHD)

2-ethyl-4-methyl-pentane-1,3-diol (EMPD)

2-ethylhexane-1,3-diol (EHD)

Despite the large number of possible products formed in the thermal treatment of an alkanal mixture, the desired 1,3-diol can in each case be obtained in high purity. When a mixture of i- and n-butyraldehydes is used, EHD can be obtained in high purity by distillation. DMHD is obtained as a further main component, while TMPD and EMPD are formed in only small amounts.

The following example illustrates the invention without implying any restriction. This example is carried out using the embodiment of the process of the present invention shown in FIG. 2.

EXAMPLE

The distillation was carried out using the residue from the preparation of i- and n-butanol, as is obtained in the process variant of FIG. 2 (stream (8)). The column (nominal bore: 45 mm) contained 6 m of CY packing (from Sulzer) and was operated batchwise at a pressure of 20 mbar at the top. The result of the distillation is shown in the table below.

|  | Temperature [° C.] | | Amount [g] 7430 | Contents (% by area in GC) | | | | |
|---|---|---|---|---|---|---|---|---|
| Fraction | Top | Bottom | Starting material | Low boilers | 2-Ethyl-hexanol 14 | DMHD 25 | EHD 35 | Remainder |
| 1 | 62–71 | 128–135 | 788 | 99.3 | 0.14 | — | — | 0.56 |
| 2 | 85 | 141–143 | 834 | 2.94 | 95.77 | 0.06 | 0.94 | 0.29 |
| 3 | 123 | 150 | 452 | 1.1 | 42.14 | 40.0 | 0.9 | 15.86 |
| 4 | 125–128 | 152–154 | 1612 | 0.22 | 0.14 | 99.1 | 0.33 | 0.23 |
| 5 | 135 | 156 | 840 | 0.79 | — | 5.48 | 93.33 | 0.4 |
| 6 | 135–136 | 157–185 | 1744 | 0.56 | — | 0.12 | 99.22 | 0.1 |
| 7 | 155 | 197 | 483 | 28.88 | 0.03 | 2.41 | 20.1 | 48.28 |
| Bottoms |  |  | 677 | — | — | 0.01 | 0.03 | 99.96 |

We claim:

1. A process for preparing 1,3-diols having six or more carbon atoms, which comprises the following steps:
   a) provision of at least one alkanal having at least three carbon atoms;
   b) thermal treatment of the alkanal in the absence of a basic catalyst;
   c) hydrogenation of the aldol addition product formed in step b); and
   d) isolation of the 1,3-diol obtained.

2. A process as claimed in claim 1, wherein the alkanal is thermally treated by subjecting it to a distillation.

3. A process as claimed in claim 2, wherein the high-boiling fraction from the distillation is subjected to the hydrogenation of step c).

4. A process as claimed in claim 1, wherein the alkanal is thermally treated by subjecting it to a hydrogenation and the 1,3-diol formed in this way is isolated.

5. A process as claimed in claim 1, wherein the alkanal has from 3 to 10 carbon atoms.

6. A process as claimed in claim 1, wherein the alkanal provided in step a) is a mixture of various isomers of an alkanal.

7. A process as claimed in claim 6, wherein the mixture is the reaction product from an oxo process.

8. A process as claimed in claim 7, wherein the mixture obtained from the oxo process is a mixture of n-butyraldehyde and i-butyraldehyde.

9. A process for preparing 2-ethylhexane 1,3-diols, in which:
   i) a mixture of n-butyraldehyde and 1-butyraldehyde is provided;
   ii) the mixture is subjected to a thermal treatment in the absence of basic catalyst by [frictionally] fractionally distilling it to give n-butyraldehyde and I-butyraldehyde;
   iii) n-butyraldehyde and 1-butyraldehyde are hydrogenated Sanol at butanol, respectively, if desired together with the distillation residue from step ii), and the hydrogenation product is subjected to a distillation, and
   iv) 2-ethylhexane-1,3-diol is isolated from the high-boiling fraction of the distillation of step iii).

10. A process as claimed in claim 1 for preparing 2-ethylhexane-1,3-diol; 2,2-dimethylhexane-1,3-diol; 2,2,4-trimethylpentane-1,3-diol; and 2-ethyl-4-methylpentane-1,3-diol, wherein:
   i) a mixture of n-butyraldehyde and i-butyraldehyde is provided;
   ii1) the mixture is subjected to a thermal treatment as per step b) and is at the same time subjected to a hydrogenation as per step c), by hydrogenating it; or
   ii2) part of the mixture from step i) is subjected to a thermal treatment as per step b) by fractionally distilling it to give n-butyraldehyde and i-butyraldehyde, and the distillation residue is, if desired together with the mixture from step i), hydrogenated; and
   iii) the hydrogenation product is subjected to a distillation and the 1,3-diols are isolated from the high-boiling fraction from the distillation.

* * * * *